(12) United States Patent
Haischmann et al.

(10) Patent No.: US 7,371,224 B2
(45) Date of Patent: May 13, 2008

(54) DEVICE FOR RINSING A BODY CAVITY

(75) Inventors: Fabian Haischmann, Berlin (DE); Thomas Merzhauser, Berlin (DE); Matthias Stiller, Berlin (DE); Martin Reuther, Berlin (DE)

(73) Assignee: W.O.M. World of Medicine AG (DE)

( * ) Notice: Subject to any disclaimer, the term of this patent is extended or adjusted under 35 U.S.C. 154(b) by 384 days.

(21) Appl. No.: 10/623,279

(22) Filed: Jul. 18, 2003

(65) Prior Publication Data

US 2004/0133149 A1    Jul. 8, 2004

(30) Foreign Application Priority Data

Jul. 19, 2002  (DE)  ............... 102 33 053
Jul. 19, 2002  (DE)  ............... 192 33 953

(51) Int. Cl.
*A61M 1/00* (2006.01)

(52) U.S. Cl. .................................................. 604/31

(58) Field of Classification Search ............... 604/119, 604/31, 35, 36, 30, 43, 150, 118, 19, 156
See application file for complete search history.

(56) References Cited

U.S. PATENT DOCUMENTS 4,755,168 A * 7/1988 Romanelli et al. ............ 604/34
4,902,277 A    2/1990 Mathies et al.
5,000,733 A    3/1991 Mathies et al.
5,336,170 A * 8/1994 Salerno et al. ................. 604/24
5,368,569 A * 11/1994 Sanese ........................ 604/113
5,630,799 A    5/1997 Beiser et al.
5,836,907 A * 11/1998 Campbell .................... 604/27
5,931,808 A    8/1999 Pike
6,024,720 A    2/2000 Chandler et al.
6,322,533 B1 * 11/2001 Gonon ......................... 604/35
2004/0034339 A1 * 2/2004 Stoller et al. .................. 606/1

* cited by examiner

*Primary Examiner*—Kevin C. Sirmons
*Assistant Examiner*—Catherine N. Witczak
(74) *Attorney, Agent, or Firm*—Allen, Dyer, Doppelt, Milbrath & Gilchrist, P.A.

(57) ABSTRACT

A device for rinsing a body cavity with a fluid includes a rinse pump for introducing fluid into a body cavity and a pressure sensor on a pressure side of the rinse pump. A medical instrument insertable into the body cavity is adapted to establish fluid communication with the body cavity. A suction pump is in fluid communication along a first pathway with the medical instrument and along a second pathway with the body cavity. Fluid flow along the second pathway is controllable. A control unit receives pressure values from the pressure sensor, controls the rinse pump, the suction pump, and the flow controller in response to received pressure values, and is thus operative to control fluid flow through the body cavity depending on an operating condition of the medical instrument.

17 Claims, 2 Drawing Sheets

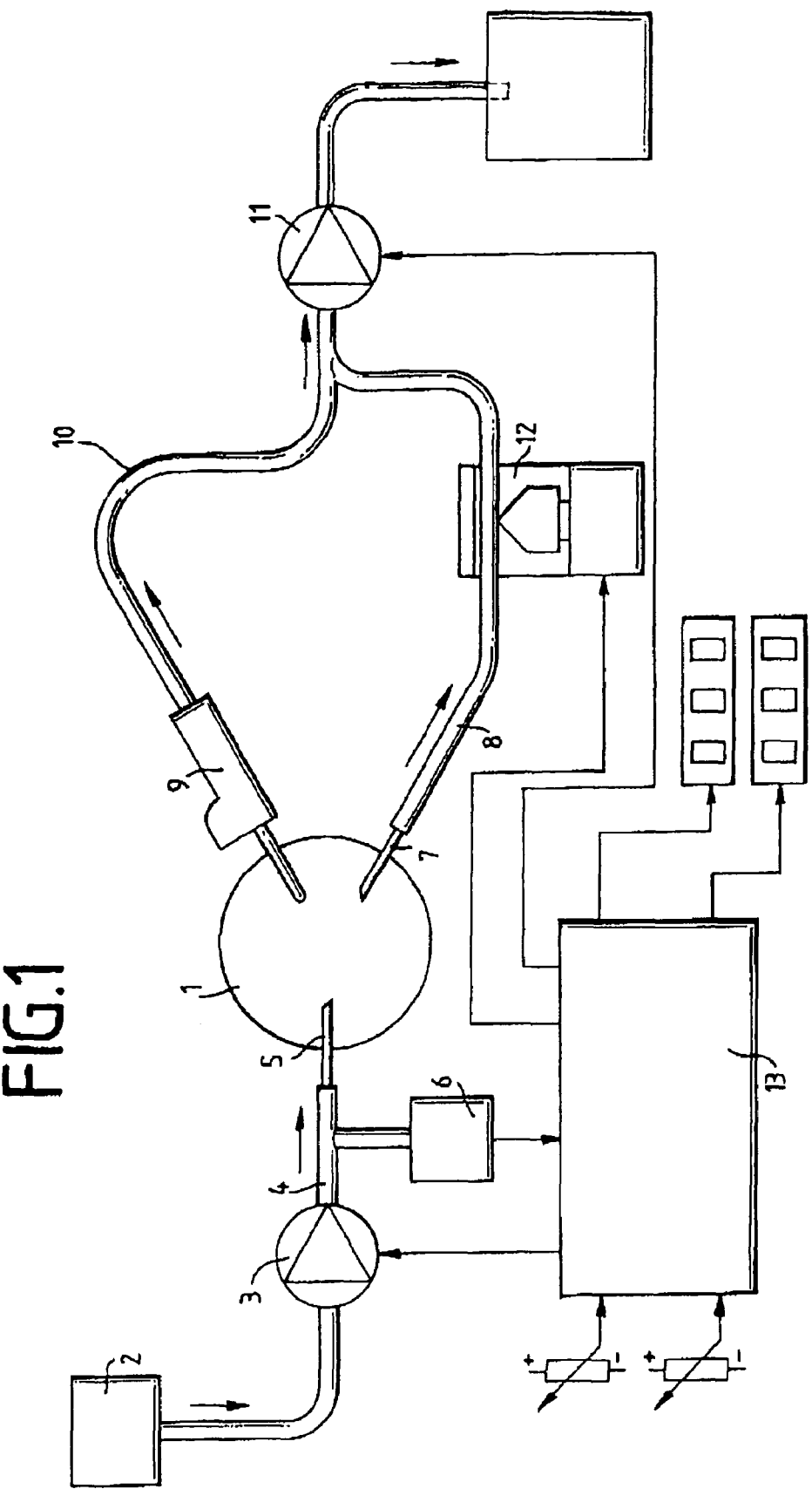

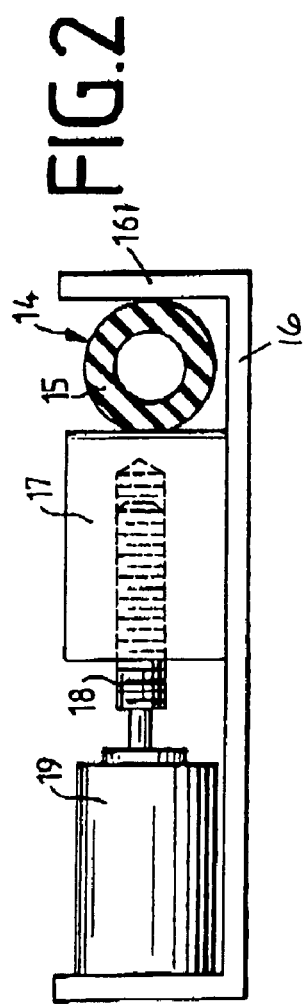
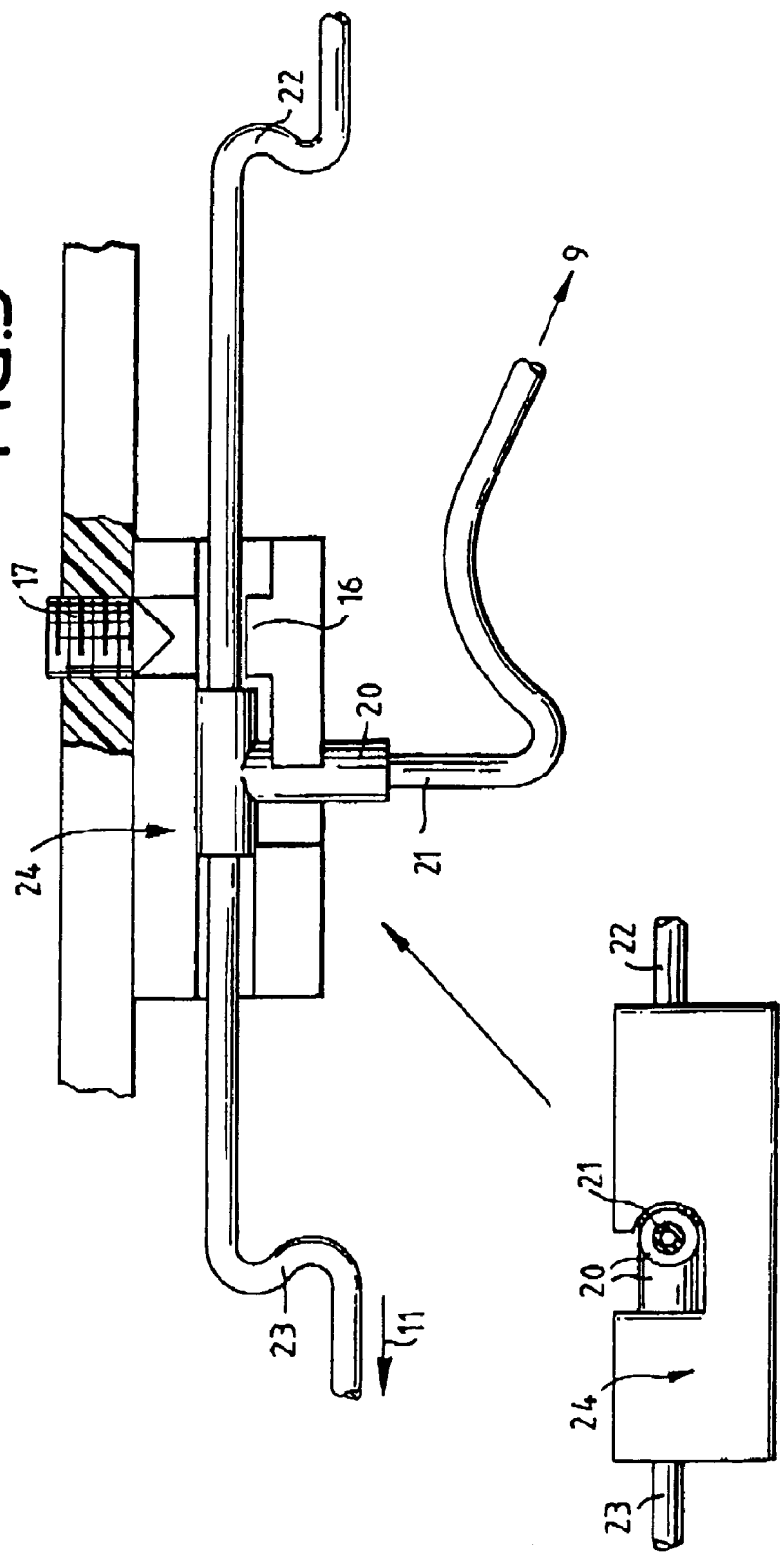

ness. FIG. 3 illustrates the hose set used according to the invention, the inset illustrating the configuration thereof.
DEVICE FOR RINSING A BODY CAVITY

CROSS-REFERENCE TO RELATED APPLICATION

This application claims priority to German application DE 102 33 053.0-35, filed Jul. 19, 2002, the contents of which are incorporated hereinto by reference.

FIELD OF THE INVENTION

The invention relates to a device and method for rinsing a body cavity with a fluid, and specifically for controlling a fluid flow therefor.

BACKGROUND OF THE INVENTION

Devices for rinsing a body cavity are known in the art wherein change-over of a suction line to preset values is performed by signal contacts of an operating unit for a medical instrument such as a shaver and application of this signal for controlling a suction/rinse device. Simultaneously, a change-over of the suction line between shaver and drainage cannula takes place.

A disadvantage of such a device is that, when a shaver is used, the operating conditions "on" and "off" are transmitted to the system by the signal contacts, typically a foot switch. In the simplest case, this may take place by signal lines having plug connections. This is expensive, in particular in construction. Furthermore, there are functional sources of faults, for instance, due to bad contacts by contact corrosion and the like. Finally, the plug connections are subject, due to frequent operation, to wear. A particularly important drawback is that the shaver must be compatible with the device, since a signal exclusively comprises the digital information "on" and "off", and consequently the control system in a control unit must be set for a second medical instrument to be employed, for instance, the shaver. If such a setting is not possible, a specific medical instrument only may be operated by the control unit. As a result, there is no compatibility between a single control unit and several different medical instruments and/or identical medical instruments of different manufacturers and different specifications with regard to the flow resistance.

Finally, it is believed disadvantageous in prior known devices that with the signaling of the operating condition from "off" to "on" of the second medical instrument on the feed side of the body cavity, an immediate increase of the flow takes place, while the increased discharge of fluid through the second medical instrument is comparatively slow. Thus a risk of a potentially medically dangerous pressure peak in the body cavity is present.

SUMMARY OF THE INVENTION

The present invention is therefore directed to providing a device, method of use, and method of making, for rinsing a body cavity with a fluid by means of which controlled flow and pressure meeting predetermined requirements is obtained, without the necessity of signal lines and independent of a second medical instrument being employed.

The device of the present invention for rinsing a body cavity with a fluid comprises a rinse pump for introducing fluid into a body cavity and a pressure sensor on a pressure side of the rinse pump. Means are provided for inserting a medical instrument into the body cavity, the medical instrument comprising means for establishing fluid communication with the body cavity. A suction pump is in fluid communication along a first pathway with the establishing means and along a second pathway with the body cavity. Means are provided for controlling fluid flow along the second pathway. A control unit is in signal communication with the rinse pump, the pressure sensor, the suction pump, and the flow controlling means. The control unit is for receiving pressure values from the pressure sensor and for controlling the rinse pump, the suction pump, and the flow controlling means in response to the received pressure values. The control unit is thus operative to control fluid flow through the body cavity depending on an operating condition of the medical instrument.

In the following, preferred embodiments of the invention are explained in more detail, with figures representing exemplary embodiments only.

BRIEF DESCRIPTION OF THE DRAWING

FIG. 1 a schematic view of the device of the present invention.

FIG. 2 a detailed schematic view of a means for varying flow resistance.

FIG. 3 illustrates the hose set used according to the invention, the inset illustrating the configuration thereof.

DETAILED DESCRIPTION OF THE PREFERRED EMBODIMENTS

In FIG. 1 can be seen a device for rinsing a body cavity 1 with a fluid. This device is provided with a storage container 2 for the fluid and with a controllable rinse pump 3 connected to the storage container 2. A supply line 4 is connected to the pressure side of the rinse pump 3. The supply line 4 is provided with a first medical instrument comprising a rinse channel 5, said first medical instrument being insertable into the body cavity 1. On the pressure side of the rinse pump 3 a pressure sensor 6 is provided for the determination of the actual pressure.

This embodiment is equipped with a drainage cannula 7 in fluid communication with a drainage line 8 insertable into the body cavity 1, and with a second medical instrument 9 insertable into the body cavity 1 and comprising a suction line 10, a controllable volume flow through the body cavity being "high" or "low", depending on the operating condition "on" or "off" of the second medical instrument 9. The drainage cannula 7 and the suction line 10 are connected to a suction pump 11. Flow through the drainage line 8 is controlled using a flow resistance controller 12. The rinse pump 3, the pressure sensor 6, and the flow resistance controller 12 are in signal communication with a control unit 13.

In FIG. 2 is illustrated a preferred embodiment of the flow resistance controller 12, comprising a hose clamping device comprising a hose 14, the hose wall 15 comprising an elastic material. The hose clamping device has a support 16 upon which the hose 14 rests, the support 16 having a wall 161, and a pressure piece 17. The pressure piece 17 is substantially perpendicular to the support wall 161, so that pressure in the direction of the support wall 161 can be exerted on the hose wall 15. The pressure piece 17 is connected by a spindle gearing 18 with an electro-motor drive 19.

In the following, the mode of operation of the invention is explained in more detail. The suction pump 11 operates with a suction capacity being equivalent, when a shaver 9 is used, to the corresponding flow in the operating condition "on" of the shaver 9, and is reduced in the operating condition "off" by the control system 13 by proportionally and continuously adjustable hose clamping 12 to the desired drainage capacity. In the operating condition "on" is formed a by-pass over the shaver 9, arranged parallel to the drainage line 8. The internal body cavity pressure is reduced due to the addition of the two volume flows through drainage line 8 and suction line 10. This pressure drop is very quickly recorded by the pressure sensor 6. The control unit 13 connected to the pressure sensor 6 detects the drop and thus detects the operating condition "on" of the shaver 9 and sends a control signal to the hose clamping device 12 to clamp the drainage line 8. Simultaneously, the rinse pump 3 is adjusted to increase the pump capacity to a pre-selected value. By control of the suction pump 11, a pressure adjustment is made by variation of the pump capacity, depending on the pre-selected pressure. This pressure may in principle and independent of this specific embodiment comprise different pre-selected values for the operating conditions of a second medical instrument 9. When the shaver 9 is switched off, the internal body cavity pressure will temporarily rise, lacking discharge flow through the suction line 10. An increase of the pressure above the pre-selected internal pressure is also recorded by the pressure sensor 6; the reverse processes take place, as described above. In the operating condition "off" of the shaver 9, the pressure can be adjusted by the pump capacity of the rinse pump 3, the pump capacity of the suction pump 11 and/or the hose clamping device 12.

Independent of the above embodiment, a determination of the actual internal pressure in the body cavity 1 may be performed by stopping the rinse pump 3 and the suction pump 11, the measured value received from the pressure sensor 6 corresponding to the actual internal pressure, owing to the static conditions (flow is virtually zero). These steps can be performed alternately with the operating condition described above. Furthermore, it is possible that differences in the measured values of the pressure sensor 6 can be used in the employed intervals (flow=pre-set, flow=0) for an internal calibration and adjustment to the first medical instrument 5 or the pressure drop thereacross. Then the control unit 13 will take these differences into account for the adjustment described above to a pre-set desired pressure value, i.e., to a relatively correspondingly higher measured value of the pressure sensor 6. This may, if applicable, also take place in a calibration curve determined after connection of a specific first medical instrument 5, so to speak "learned", and stored in the control unit 13. It is recommended that "learning" be performed after connecting a first medical instrument and prior to or at the beginning of a treatment.

FIG. 3 illustrates a hose set for a device according to the invention, comprising a T piece 20 and hoses 21, 22, 23 connected to said T piece 20, wherein a first hose 21 is intended for the connection to the second medical instrument 9, a second hose 22 forms at least part of the drainage line 8, and a third hose 23 is intended for the connection to the suction pump 11. As an option the first hose 21 and the third hose 23 are made from a polymer having a hardness of at least shore A 70, preferably 75, and the second hose 22 is made from a polymer having a hardness of less than shore A 70, preferably 65. The T piece 20 is made from an inherently stable plastic material and is adapted in a positive locking manner complementarily to a T piece positive locking cutout 24 provided as one unit together with a flow resistance controller 12. This unit is, if applicable, releasably attached to a device wall in turn supporting the drive means 19 for the pressure piece 17, by which the pressure piece 17 is drivable against the support wall 161 and thus clamps the second hose 22 down. It is understood that the second hose 22 preferably has, at least in the area between the pressure piece 17 and the support wall 161, the aforementioned lower shore hardness. Insertion of the T piece 20 into the T piece positive locking cutout 24 and fixation therein immediately follow from examination of FIG. 3.

In an alternative method of operation of a device according to the invention, the suction pump 11 operates with an adjustable suction capacity (flow, speed) predetermined to a value appropriate for the second medical instrument, e.g., shaver 9, but not dependent on the actual pressure in the internal body cavity 1. The suction pump 11 is, instead, continuously operated by the control unit 13 at a speed that corresponds to the desired flow through the second medical instrument 9 when activated. Accordingly, a reduced pressure is created in the hoses 8,10 between the suction pump 11, second medical instrument 9, and the flow resistance controller 12. When the second medical instrument 9 is activated, the flow through the second medical instrument 9 rises from a minimum value or from zero to an operating level, wherein the operating flow depends on the suction pump 11 speed adjustment selected by an operator or predetermined otherwise, e.g., by programming of the control unit 13. The increased flow through the second medical instrument 9 (wherein the position of the flow resistance controller 12 remains the same at least initially) leads to a pressure drop in the body cavity 1. Upon detection of this pressure drop by the pressure sensor 6, the control unit 13 increases the flow through the rinse pump 11, e.g., the speed thereof, in order to compensate for the pressure drop. If this increased rinse pump 11 flow does not achieve full compensation for the pressure drop (i.e., recovery of the pressure in the body cavity 1 before activation of the second medical instrument 9), the control unit 13 further controls the flow resistance controller 12 to increase the flow resistance and thus to reduce the total flow from the body cavity 1 to the suction pump 11. The latter feature comprises operating the flow resistance controller 12 below maximum flow resistance when the second medical instrument 9 is not activated.

The present invention provides that a decrease of the actual pressure measured by the pressure sensor 6 from a given required pressure can be detected, when the second medical instrument is changed from "off" to "on", providing for the issuance of a control signal for the flow resistance controller 12, the rinse pump 3, and/or the suction pump 11, and that according to a pre-set required feed capacity of the rinse pump and/or of the suction pump for the operating condition "on" and to the required pressure, and vice versa.

In other words, in for instance the operating condition "off" of a shaver 9, suction of the fluid from the body cavity 1 essentially takes place through the drainage line 8. By changing the shaver 9 to operating condition "on", so to speak a by-pass, the suction line 10 to the drainage line 8 is activated, with the consequence of a (temporary) pressure drop in the body cavity. This pressure drop is detected, with the consequence that the flow is increased by the control action of the rinse pump 3 to a pre-selected value (higher than for shaver "off"). The pressure control may then with constant flow take place by means of control of the suction pump 11.

The present invention achieves that the flow and the pressure in the body cavity 1 can freely and independently of each other be controlled and held constant, irrespective of the operating condition of the second medical instrument 9. Control of the flow is more rapidly performed with this invention for a variation of flow resistance than with a speed-controlled roller pump, due to the smaller weights and moments of inertia of the flow resistance controller 12. The adaptation of the flow and, if necessary, the setting and re-adjustment of the pressure takes place according to the operating condition "on" or "off" of the second medical instrument 9. It is also advantageous that pressure variations in the body cavity 1 are detected by the system in a very short time and can be corrected to the desired pressure value, so that the pressure in the body cavity 1 is also held virtually constant, when the operating conditions of the second medical instrument 9 are changed. Another advantage is that any medical instrument can be used, without expensive adaptations of signal lines and plug connections, since control and regulation mechanisms provide in every case for setting and holding the pre-set values of pressure and flow constant. Finally, the arrangement of the flow resistance controller 12 in conjunction with the drainage line 8 is advantageous, since the pressure and flow regulation follow the switching on of the medical instrument, thus avoiding pressure peaks that can potentially represent health risks. Simultaneously, any leakages due to the delay of the regulation are automatically and without additional measures detected. Finally, a virtually constant body cavity distension and correspondingly with an endoscopic optical system can be achieved.

The first medical instrument 5 may be selected from a group including a rinse probe, rinse cannula, trocar with optical system, and optical system with rinse channel, although these are not intended as limitations.

The rinse pump 3 may comprise a drive unit having a motor with a rotating driven shaft and a pump unit (mechanically, i.e., by self substance, positive locking, or force locking, or magnetically, i.e., by force locking) connected to the drive shaft and rotationally driven, the feed capacity being controllable by varying the speed of the motor. In particular, this may be a peristaltic pump. Alternatively, the rinse pump 3 may comprise an elastic storage container with a controllable pressure cuff fully or partially surrounding the storage container, the feed capacity being controllable by regulation of the pressure cuff. Finally, the rinse pump 3 may further comprise a height level-variable storage container, the feed capacity being controllable by regulation of the height level of the storage container.

The second medical instrument 9 may be selected from a group including a shaver, sampling device, and suction probe, although these are not intended as limitations. In particular in the case of a shaver, it is recommended that in the operating condition "on", the volume flow through the second medical instrument 9 be "high" and vice versa. However, the opposite relation may also be possible.

In principle, the control unit and the components connected thereto may be operated or controlled hydraulically, pneumatically, or electrically, with electrical or electromechanical operation being preferred.

The flow resistance controller 12 may be controllable proportionally, continuously, or in a multitude of discrete steps. It is preferred that the flow resistance controller comprise a hose clamping device with a hose as discussed above. The hose walls preferable comprise an elastic material. In detail, the flow resistance controller 12 may comprise a support surface upon which the hose wall rests, and may be provided with a pressure piece, by means of which pressure in the direction of the support surface is exerted on the hose wall. It is preferred that the pressure piece be linearly drivable and connected by a spindle gearing to an electro-motor drive, preferably a stepping motor. Depending on the control and regulation characteristic, nonlinear functions between a control signal and the movement of the pressure piece may, however, also be provided. An example for this is a rotating, linearly driven round eccentric disk the surface of which runs against the hose wall or a pressure piece. By means of a cam, any desired kinematics may be achieved.

It is recommended that the drainage line 8 and the suction line 10 or the suction pump 11, respectively, terminate in a collection vessel 25.

The invention further teaches a method for the operation of a device according to the invention, wherein at changeover of a second medical instrument 9 between two operating conditions correlated with different flows in the suction line 10, by means of a pressure sensor 6 and the control unit 13 a pressure variation can be detected. By means of the control unit 13, upon detection of a pressure variation, the flow resistance controller is activated according to an adjustment to a given desired flow and/or pressure associated with the active operating condition of the second medical instrument 9. With regard to adjustment processes, it is recommended that upon a detection of a pressure variation, additionally the rinse pump 3 and/or the suction pump 11 are activated by the control unit 13 according to the adjustment to a given desired flow and/or pressure associated with the active operating condition of the second medical instrument 9.

Such devices may be, for instance, employed for endoscopic examinations and distension or resection of tissues, in particular under endoscopic control. A body cavity may be a cavity of a joint, for instance, a knee or a shoulder joint, a cavity between muscles or organs, or an organ itself forming or comprising a cavity. A fluid is in particular a liquid. This may be a homogeneous liquid phase or also a dispersion or an emulsion. A drainage cannula may perform, in addition to the drainage function, further functions, as for instance an illumination of the body cavity by a light source integrated in the drainage cannula. Different volume flows with different operating positions are differentiated, in the meaning of the invention, by the terms "high" and "low", the absolute values being irrelevant. These terms serve for nothing more than indicating how the volume flows are relative to each other in the respective operating conditions of the second medical instrument.

What is claimed is:

1. A device for rinsing a body cavity with a fluid comprising:
   a rinse pump operative to introduce fluid into a body cavity through a channel,
   a pressure sensor on a pressure side of the rinse pump and upstream of an outlet of the channel;
   means for inserting a medical instrument into the body cavity, the medical instrument comprising means for establishing fluid communication with the body cavity;
   a suction pump in fluid communication along a first pathway with the fluid communication establishing means and along a second pathway with the body cavity;
   a T piece and a first, a second, and a third hose connected to outlets of the T piece, the first pathway comprising the first hose connected to an outlet of the medical instrument, the second pathway comprising the second hose, and the third hose connected to the suction pump;
   means for controlling fluid flow along the second pathway;
   a T piece positive locking cutout having a recess adapted to positively lock the T piece thereinto, the T piece positive locking cutout integrally formed with the fluid flow controlling means; and a control unit in signal communication with the rinse pump, the pressure sensor, the suction pump, and the fluid flow controlling means, for receiving pressure values from the pressure sensor and for controlling the rinse pump, the suction pump, and the fluid flow controlling means in response to the received pressure values, operative to control fluid flow through the body cavity depending on received pressure changes caused by changes in an operating condition of the medical instrument according to a preset volume flow of at least one of the rinse pump and the suction pump and according to a predetermined required pressure.

2. The device recited in claim 1, wherein the rinse pump comprises an elastic storage container and a controllable pressure cuff at least partially surrounding the storage container, a feed capacity of the rinse pump controllable by regulation of the pressure cuff.

3. The device recited in claim 2, further comprising a storage container in fluid communication with an inlet side of the rinse pump, for supplying the fluid to be introduced into the body cavity.

4. The device recited in claim 2, wherein the medical instrument comprises a second medical instrument, and further comprising a first medical instrument in fluid communication with the rinse pump for introducing the fluid into the body cavity therefrom.

5. The device recited in claim 4, the first medical instrument is selected from a group consisting of a rinse probe, a trocar and an optical system, and an optical system, rinse channel, and rinse cannula.

6. The device recited in claim 2, wherein the second pathway comprises a drainage cannula insertable into the body cavity and a drainage line in fluid communication with an outlet of the drainage cannula and with the fluid flow controlling means.

7. The device recited in claim 2, wherein the medical instrument has an "on" and an "off" operating condition.

8. The device recited in claim 7, wherein the medical instrument further has a "high" and a "low" volume flow depending on the operating condition.

9. The device recited in claim 8, wherein, when the medical instrument has an "on" operating condition, the volume flow is "high," and, when the medical instrument has an "off" operating condition, the volume flow is "low."

10. The device recited in claim 2, wherein the rinse pump comprises a drive unit having a motor having a rotating driven shaft and a pump unit, a feed capacity of the rinse pump controllable by varying the speed of the motor.

11. The device recited in claim 2, wherein the rinse pump comprises a height level-variable storage container, a feed capacity of the rinse pump controllable by regulation of the height level of the storage container.

12. The device recited in claim 2, wherein the medical instrument is selected from a group consisting of a shaver, a sampling device, and a suction probe.

13. The device recited in claim 2, wherein the fluid flow controlling means are operable to control flow along the second pathway in one of the modes of proportionally, continuously, or in a multitude of discrete steps.

14. The device recited in claim 2, wherein the fluid flow controlling means comprises a hose clamping device comprising a hose having a wall at least partially comprising an elastic material, a support surface for supporting the hose thereupon, and a pressure piece positioned on an opposite side of the hose from the support surface, the pressure piece drivable toward and away from the support surface for exerting and decreasing pressure on the elastic portion of the hose wall.

15. The device recited in claim 14, wherein the pressure piece is substantially linearly drivable.

16. The device recited in claim 15, further comprising an electro-motor drive having a spindle gearing connected to the pressure piece.

17. The device recited in claim 16, wherein the electro-motor drive comprises a stepping motor.

* * * * *